United States Patent [19]

Wagle et al.

[11] Patent Number: 5,698,563

[45] Date of Patent: Dec. 16, 1997

[54] BIS-[HYDRAZONES]

[75] Inventors: Dilip R. Wagle, Valley Cottage, N.Y.; Michael E. Lankin, Montclair; David H. Shih, Lawrenceville, both of N.J.

[73] Assignee: Alteon Inc., Ramsey, N.J.

[21] Appl. No.: 372,672

[22] Filed: Jan. 13, 1995

[51] Int. Cl.[6] ................... A61K 31/415; A61K 31/505
[52] U.S. Cl. .................. 514/275; 514/392; 544/296;
544/331; 548/312.7; 548/313.1; 564/227;
564/228
[58] Field of Search ..................... 544/296, 331;
514/275, 392; 548/312.7, 313.1

[56] References Cited

U.S. PATENT DOCUMENTS

| | | | |
|---|---|---|---|
| 4,520,031 | 5/1985 | Knight, III | 514/632 |
| 4,758,583 | 7/1988 | Cerami et al. | 514/399 |
| 5,258,381 | 11/1993 | Ulrich et al. | 514/235.8 |
| 5,399,560 | 3/1995 | Cerami et al. | 514/242 |

FOREIGN PATENT DOCUMENTS

| | | |
|---|---|---|
| 018850 | 11/1980 | European Pat. Off. . |
| 316852 | 5/1989 | European Pat. Off. . |
| WO 94/11490 | 5/1994 | WIPO . |

OTHER PUBLICATIONS

Balana–Fouce et al. (1986) Comp. Biochem. Physiol. 83c:419–21.
Hibasami et al. (1988) Cancer Chemother. Pharmacol. 22:187–90.
Lukkari et al. (1992) J. Pharm. Biomed. Anal. 10:561–5.
Murdock et al. (1993) J. Med. Chem. 36:2098–101.
Nakashima et al. (1987) Eur. J. Med. Chem. 22:553–8.
Nishimura et al. (1977) Kitasato Arch. Exp. Med. 50:31–8.
Rodriguez et al. (1993) J. Vet. Pharmacol. Ther. 16:241–4.
Tognon et al. (1984) Proc. Natl. Acad. Sci. USA 81:2440–3.
Brownlee et al. 1986. "Aminoguanidine prevents diabetes–induced arterial wall protein cross–linking." Science 232: 1629–32.
Brownlee et al. 1986. "Inhibition of glucose–derived protein crosslinking and prevention of early diabetic changes in glomerular basement membrane by aminoguanidine." Diabetes 35: supp. 1: 42A, 166.
Bucala and Cerami. 1992. "Advanced Glycosylation; Chemistry, Biology, and Implications for Diabetes and Aging" in *Advances in Pharmacology*. vol. 23. pp. 1–34, Academic Press.
Eble et al. 1983. "Nonenzymatic Glucosylation and Glucose–dependent Crosslinking of Protein". J. Biol. Chem. 258:9406–9412.
Hayase et al. 1989. "Aging of proteins: immunological detection of a glucose–derived pyrrole formed during Maillard reaction in vivo." J. Biol. Chem. 263: 3758–64.
Nicholls and Mandel. 1989. "Advanced glycosylation end–products in experimental murine diabetic nephropathy." Lab. Invest. 60: 486–91.
Nordbo. 1978. "Ability of chlorhexidine and benzalkonium chloride to catalyze browning reactions in vivo." J. Dent. Res. 58: 1429.
Oimomi et al. 1989. "Letter to the editor re: Aminoguanidine inhibits 3–deoxyglucosone during the advanced Maillard reaction." Diabetes Res. Clin. Prac. 6: 311–33.
Oimomi et al. 1989 "The effects of aminoguanidine on 3–deoxyglucosone in the Maillard reaction." Agric. Biol. Chem. 53: 1727–8.
Sell and Monnier. 1989. "Structure elucidation of a senescence cross–link from a human extracellular matrix." J. Biol. Chem. 264: 21597–602.
Sidzhakova et al, Analytical Laboratory, 3(4) (1994), pp. 228–234.
Sidhakova et al, Chemical Abstract 123: 96297 (1994).
Sidhakova et al, Pharmazie 48(6), (1993), pp. 417–419.

*Primary Examiner*—Philip I. Datlow
*Attorney, Agent, or Firm*—Klauber & Jackson

[57] ABSTRACT

The present invention relates to compositions and methods for inhibiting nonenzymatic cross-linking (protein aging). Accordingly, a composition is disclosed which comprises bis(guanylhydrazone) of the formula

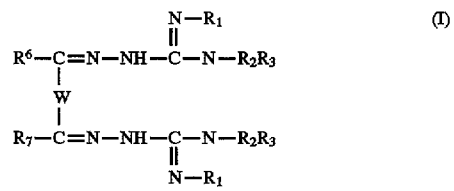

capable of inhibiting the formation of advanced glycosylation endproducts of target proteins by reacting with the carbonyl moiety of the early glycosylation product of such target proteins formed by their initial glycosylation. The method comprises contacting the target protein with the composition. Both industrial and therapeutic applications for the invention are envisioned, as food spoilage and animal protein aging can be treated.

27 Claims, No Drawings

BIS-[HYDRAZONES]

BACKGROUND OF THE INVENTION

The present invention relates generally to the aging of proteins resulting from their reaction with glucose and other reducing sugars, and more particularly to the inhibition of the reaction of nonenzymatically glycosylated proteins and the often resultant formation of advanced glycosylation (glycation) end products and cross-links.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. The reaction has also been found to occur with a variety of other body proteins, such as lens crystallins, collagen and nerve proteins. See Bucala et al., "Advanced Glycosylation; Chemistry, Biology, and Implications for Diabetes and Aging" in *Advances in Pharmacology*, Vol. 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In U.S. Pat. No. 4,758,583, a method and associated agents were disclosed that served to inhibit the formation of advanced glycosylation endproducts by reacting with an early glycosylation product that results from the original reaction between the target protein and glucose. Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility.

SUMMARY OF THE INVENTION

In accordance with the present invention, a method and compositions are disclosed for the inhibition of the advanced glycosylation of proteins (protein aging). In particular, the compositions comprise agents for inhibiting nonenzymatic cross-linking (protein aging) due to the formation of advanced glycosylation (glycation) endproducts. The agents may be selected from those materials capable of reacting with an early glycosylation product from the reaction of glucose with proteins and preventing further reactions. Cross-linking caused by other reactive sugars present in vivo or in foodstuffs, including ribose, galactose and fructose would also be prevented by the methods and compositions of the present invention.

The agents comprise bis-guanylhydrazone compounds having the following structural formula:

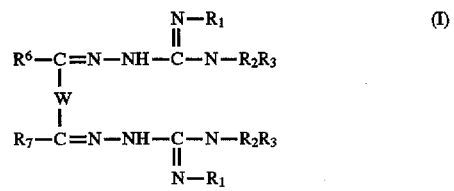

wherein $R_1$ and $R_2$ are each hydrogen or, together, are an alkylene group of 2–3 carbon atoms, or, when $R_1$ is hydrogen, then $R_2$ can be a group of the formula

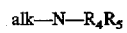

wherein alk is a straight or branched chain alkylene group of 1–8 carbon atoms, and $R_4$ and $R_5$ are independently each a lower alkyl group of 1–6 carbon atoms, or together with the nitrogen atom form a morpholino, piperdinyl or methylpiperazinyl group;

$R_3$ is hydrogen, or when $R_1$ and $R_2$ are together an alkylene group of 2–3 carbon atoms, a hydroxyethyl group;

W is a carbon-carbon bond or an alkylene group of 1–3 carbon atoms, and $R_6$ is a lower alkyl, aryl, or heteroaryl group and $R_7$ is hydrogen, a lower alkyl, aryl or heteroaryl group; with the proviso that when W is a carbon-carbon bond, then $R_6$ and $R_7$ together can also be a 1,4-butylene group;

or W is a 1,2-, 1,3-, or 1,4-phenylene group, optionally substituted by one or two lower alkyl or amino groups, a 2,3-naphthylene group; a 2,5-thiophenylene group; or a 2,6-pyridylene group; and $R_6$ and $R_7$ are both hydrogen or a lower alkyl group;

or W is an ethylene group and $R_6$ and $R_7$ together are an ethylene group;

or W is an ethenylene group and $R_6$ and $R_7$ together are an ethenylene group;

or W is a methylene group and $R_6$ and $R_7$ together are a group of the formula

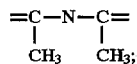

or —C—W—C— and $R_6$ and $R_7$ together form a bicyclo-(3,3,1)-nonane or a bicyclo-3,3,1-octane group and $R_1$ and $R_2$ are together an alkylene group of 2–3 carbon atoms and $R_3$ is hydrogen;

and their biologically or pharmaceutically acceptable acid addition salts; and mixtures thereof, and a carrier therefor.

The compounds, and their compositions, utilized in this invention appear to react with an early glycosylation product thereby preventing the same from later forming the advanced glycosylation end products which lead to protein cross-links, and thereby, to protein aging.

The present invention also relates to a method for inhibiting protein aging by contacting the initially glycosylated protein at the stage of the early glycosylation product with a quantity of one or more of the agents of the present invention, or a composition containing the same. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

The ability to inhibit the formation of advanced glycosylation endproducts carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts carries the promise of treatment for diabetes and, of course, improving the quality and, perhaps, duration of animal life.

The present agents are also useful in the area of personal appearance and hygiene, as they prevent the staining of teeth by cationic anti-microbial agents with anti-plaque properties, such as chlorhexidine.

Accordingly, it is a principal object of the present invention to provide a method for inhibiting the extensive cross-linking of proteins that occurs as an ultimate consequence of the reaction of the proteins with glucose and other reactive sugars, by correspondingly inhibiting the formation of advanced glycosylation endproducts.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a still further object of the present invention to provide therapeutic methods of treating the adverse consequences of protein aging by resort to the aforesaid method and agents.

It is a still further object of the present invention to provide a method of inhibiting the discoloration of teeth by resort to the aforesaid method and agents.

It is a still further object of the present invention to provide compositions including pharmaceutical compositions, all incorporating the agents of the present invention.

It is still further object of the present invention to provide novel compounds, as well as processes for their preparation, for use in the methods and compositions of the present invention.

Other objects and advantages will become apparent to those skilled in the art from a consideration of the ensuing description.

DETAILED DESCRIPTION OF THE PREFERRED EMBODIMENT

In accordance with the present invention, agents, compositions including pharmaceutical compositions containing said agents and associated methods have been developed which are believed to inhibit the formation of advanced glycosylation endproducts in a number of target proteins existing in both animals and plant material. In particular, the invention relates to a composition which may contain one or more agents comprising bisguanylhydrazone compounds having the structural formula

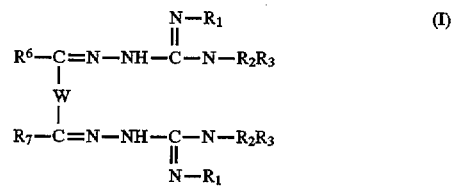

wherein
$R_1$ and $R_2$ are each hydrogen or, together, are an alkylene group of 2–3 carbon atoms, or, when $R_1$ is hydrogen, then $R_2$ can be a group of the formula

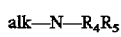

wherein alk is a straight or branched chain alkylene group of 1–8 carbon atoms, and $R_4$ and $R_5$ are independently each a lower alkyl group of 1–6 carbon atoms, or together with the nitrogen atom form a morpholino, piperdinyl or methylpiperazinyl group;

$R_3$ is hydrogen, or when $R_1$ and $R_2$ are together an alkylene group of 2–3 carbon atoms, a hydroxyethyl group;

W is a carbon-carbon bond or an alkylene group of 1–3 carbon atoms, and $R_6$ is a lower alkyl, aryl, or heteroaryl group and $R_7$ is hydrogen, a lower alkyl, aryl or heteroaryl group; with the proviso that when W is a carbon-carbon bond, then $R_6$ and $R_7$ together can also be a 1,4-butylene group;

or W is a 1,2-, 1,3-, or 1,4-phenylene group, optionally substituted by one or two lower alkyl or amino groups, a 2,3-naphthylene group; a 2,5-thiophenylene group; or a 2,6-pyridylene group; and $R_6$ and $R_7$ are both hydrogen or a lower alkyl group;

or W is an ethylene group and $R_6$ and $R_7$ together are an ethylene group;

or W is an ethenylene group and $R_6$ and $R_7$ together are an ethenylene group;

or W is a methylene group and $R_6$ and $R_7$ together are a group of the formula

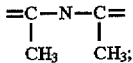

or —C—W—C— and $R_6$ and $R_7$ together form a bicyclo-(3,3,1)-nonane or a bicyclo-3,3,1-octane group and $R_1$ and $R_2$ are together an alkylene group of 2–3 carbon atoms and $R_3$ is hydrogen;

and their biologically or pharmaceutically acceptable acid addition salts; and mixtures thereof, and a carrier therefor.

The lower alkyl groups referred to above preferably contain 1–6 carbon atoms and include methyl, ethyl, propyl, butyl, pentyl, hexyl, and the corresponding branched-chain isomers thereof. These groups are optionally substituted by one or more halo hydroxy, amino or lower alkylamino groups.

The alkylene groups referred to herein likewise can be straight or branched chain, and are thus exemplified by ethylene, propylene, butylene, pentylene, hexylene, and their corresponding branched chain isomers.

The aryl groups encompassed by the above formula are those containing 6–10 carbon atoms, such as phenyl and lower alkyl substituted-phenyl, e.g. tolyl and xylyl, and are optionally substituted by 1–2 halo, hydroxy or lower alkoxy groups.

The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like.

The heteroaryl groups referred to in the above formula contain 1–2 heteroatoms, i.e. nitrogen, oxygen or sulfur, and are exemplified by be furyl, pyrrolinyl, pyridyl, pyrimidinyl, thienyl, quinolyl, and the corresponding alkyl substituted compounds.

For the purposes of this invention equivalent to the compounds of formula (I) are the biologically and pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by Formula I, certain substituents are preferred. For instance, the compounds wherein $R_2$ and $R_3$ are together an alkylene group of 2–3 carbon atoms are preferred. The compounds wherein $R_6$ and $R_7$ together are a butylene, ethylene, or an ethenylene group and those wherein $R_6$ and $R_7$ are both methyl or furyl groups are also highly preferred.

Representative compounds of the present invention are:

methyl glyoxal bis(guanylhydrazone);
methyl glyoxal bis(2-hydrazino-2-imidazoline-hydrazone);
terephthaldicarboxaldehyde bis(2-hydrazino-2-imidazoline hydrazone);
terephaldicarboxaldehyde bis(guanylhydrazone);
phenyl glyoxal bis(2-hydrazino-2-imidazoline hydrazone);
furyl glyoxal bis(2-hydrazino-2-imidazoline hydrazone);
methyl glyoxal bis[1-(2-hydroxyethyl)-2-hydrazino-2-imidazoline hydrazone];
methyl glyoxal bis[1-(2-hydroxyethyl)-2-hydrazino-1,4,5,6-tetrahydropyrimidine hydrazone];
phenyl glyoxal bis(guanylhydrazone);
phenyl glyoxal bis[1-(2-hydroxyethyl)-2-hydrazino-2-imidazoline hydrazone];
furyl glyoxal bis[1-(2-hydroxyethyl)-2-hydrazino-2-imidazoline hydrazone];
phenyl glyoxal bis[1-(2-hydroxyethyl)-2-hydrazino-1,4,5,6-tetrahydropyrimidine hydrazone];
furyl glyoxal bis[1-(2-hydroxyethyl)-2-hydrazino-1,4,5,6-tetrahydropyrimidine hydrazone];
2,3-butanedione bis(2-hydrazino-2-imidazoline hydrazone);
1,4-cyclohexane dione bis(2-hydrazino-2-imidazoline hydrazone];
o-phthalic dicarboxaldehyde bis(2-hydrazino-2-imidazoline hydrazone);
2,3-naphthalene dialdehyde bis(2-hydrazino-2-imidazoline hydrazone);
1,2-cyclohexanedione bis(2-hydrazino-2-imidazoline hydrazone);
2,4-pentanedione bis(2-hydrazino-2-imidazoline hydrazone);
furyl bis(2-hydrazino-2-imidazoline hydrazone);
1,4-benzoquinone bis(2-hydrazino-2-imidazoline hydrazone);
methyl glyoxal bis(2-hydrazino-1,4,5,6-tetrahydropyrimidine hydrazone);
methyl glyoxal bis[N-(2,2-dimethyl-3-dimethylaminopropyl)hydrazinecarboximidamide hydrazone];
methyl glyoxal bis[N-3-dimethylaminopropyl) hydrazinecarboximidamide hydrazone];
methyl glyoxal bis{N-[2-(4-morpholino)ethyl] hydrazinecarboximidamide hydrazone}; and
methyl glyoxal bis{N-[3-(4-methylpiperazin-1-yl)propyl] hydrazinecarboximidamide hydrazone};
furyl glyoxal bis (guanyl hydrazone)dihydrochloride dihydrate;
2,3-pentanedione bis(2-tetrahydropyrimidine)hydrazone dihydrobromide;
1,2-cyclohexanedione bis(2-tetrahydropyrimidine) hydrazone dihydrobromide;
2,3-hexanedione bis(2-tetrahydropyrimidine)hydrazone dihydrobromide;
1,3-diacetyl bis(2-tetrahydropyrimidine)hydrazone dihydrobromide;
2,3-butanedione bis(2-tetrahydropyrimidine)hydrazone dihydrobromide;
2,6-diacetylpyridine-bis-(2-hydrazino-2-imidazoline hydrazone)dihydrobromide;
2,6-diacetylpyridine-bis-(guanyl hydrazone) dihydrochloride;
2,6-pyridine dicarboxaldehyde-bis-(2-hydrazino-2-imidazoline hydrazone)dihydrobromide trihydrate);
2,6-pyridine dicarboxaldehyde-bis(guanyl hydrazone) dihydrochloride;
1,4-diacetyl benzene-bis-(2-hydrazino-2-imidazoline hydrazone)dihydrobromide dihydrate;
1,3-diacetyl benzene-bis-(2-hydrazino-2-imidazoline) hydrazone dihydrobromide;
1,3-diacetyl benzene-bis(guanyl)-hydrazone dihydrochloride;
isophthalaldehyde-bis-(2-hydrazino-2-imidazoline) hydrazone dihydrobromide;
isophthalaldehyde-bis-(guanyl)hydrazone dihydrochloride;
2,6-diacetylaniline bis-(guanyl)hydrazone dihydrochloride;
2,6-diacetyl aniline bis-(2-hydrazino-2-imidazoline) hydrazone dihydrobromide;

2,5-diacetylthiophene bis(guanyl)hydrazone dihydrochloride;

2,5-diacetylthiophene bis-(2-hydrazino-2-imidazoline) hydrazone dihydrobromide;

1,4-cyclohexanedione bis(2-tetrahydropyrimidine) hydrazone dihydrobromide;

3,4-hexanedione bis(2-tetrahydropyrimidine)hydrazone dihydrobromide;

methyl glyoxal-bis-(4-amino-3-hydrazino-1,2,4-triazole) hydrazone dihydrochloride;

methyl glyoxal-bis-(4-amino-3-hydrazino-5-methyl-1,2,4-triazole)hydrazone dihydrochloride;

2,3-pentanedione-bis-(2-hydrazino-3-imidazoline) hydrazone dihydrobromide;

2,3-hexanedione-bis-(2-hydrazino-2-imidazoline) hydrazone dihydrobromide;

3-ethyl-2,4-pentane dione-bis-(2-hydrazino-2-imidazoline) hydrazone dihydrobromide;

methyl glyoxal-bis-(4-amino-3-hydrazino-5-ethyl-1,2,4-triazole)hydrazone dihydrochloride;

methyl glyoxal-bis-(4-amino-3-hydrazino-5-isopropyl-1,2,4-triazole)hydrazone dihydrochloride;

methyl glyoxal-bis-(4-amino-3-hydrazino-5-cyclopropyl-1,2,4-triazole)hydrazone dihydrochloride;

methyl glyoxal-bis-(4-amino-3-hydrazino-5-cyclobutyl-1,2,4-triazole)hydrazone dihydrochloride;

1,3-cyclohexanedione-bis-(2-hydrazino-2-imidazoline) hydrazone dihydrobromide;

3,5-diacetyl-1,4-dihydro-2,6-dimethyl pyridine bis(guanyl) hydrazone dihydrochloride;

3,5-diacetyl-1,4-dihydro-2,6-dimethyl pyridine bis-(2-hydrazino-2-imidazoline)hydrazone dihydrobromide;

bicyclo-(3,3,1)nonane-3,7-dione bis-(2-hydrazino-2-imidazoline)hydrazone dihydrobromide; and cis-bicyclo(3,3,1)octane-3,7-dione bis-(2-hydrazino-2-imidazoline) hydrazone dihydrobromide.

Certain of the compounds represented by Formula I are novel compounds which represent a further embodiment of the present invention. These compounds are represented by the formula

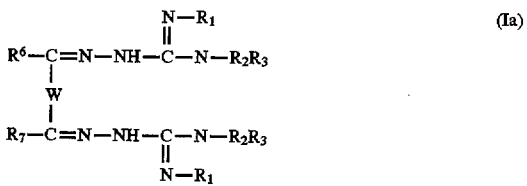

wherein $R_1$ and $R_2$ are each hydrogen or, together, are an alkylene group of 2–3 carbon atoms, or, when $R_1$ is hydrogen, then $R_2$ can be a group of the formula alk—N—$R_4R_5$ wherein alk is a straight or branched chain alkylene group of 1–8 carbon atoms, and $R_4$ and $R_5$ are independently each a lower alkyl group of 1–6 carbon atoms, or together with the nitrogen atom form a morpholino, piperdinyl or methylpiperazinyl group;

$R_3$ is hydrogen, or when $R_1$ and $R_2$ are together an alkylene group of 2–3 carbon atoms, a hydroxyethyl group;

W is a carbon-carbon bond or an alkylene group of 1–3 carbon atoms, and $R_6$ is a lower alkyl, aryl, or heteroaryl group and $R_7$ is hydrogen, a lower alkyl, aryl or heteroaryl group; with the proviso that when W is a carbon-carbon bond, then $R_6$ and $R_7$ together can also be a 1,4-butylene group; and with the further proviso that when W is a carbon-carbon bond and $R_6$ or $R_7$ is lower alkyl, then at least one of $R_1$, $R_2$, and $R_3$ must be other than hydrogen;

or W is a 1,2-, 1,3-, or 1,4-phenylene group, optionally substituted by one or two lower alkyl or amino groups, a 2,3-naphthylene group; a 2,5-thiophenylene group; or a 2,6-pyridylene group; and $R_6$ and $R_7$ are both hydrogen or a lower alkyl group;

or W is an ethylene group and $R_6$ and $R_7$ together are an ethylene group;

or W is an ethenylene group and $R_6$ and $R_7$ together are an ethenylene group;

or W is a methylene group and $R_6$ and $R_7$ together are a group of the formula

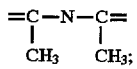

or —C—W—C— and $R_6$ and $R_7$ together form a bicyclo (3,3,1)-nonane or a bicyclo-3,3,1-octane group and $R_1$ and $R_2$ are together an alkylene group of 2–3 carbon atoms and $R_3$ is hydrogen;

and their biologically or pharmaceutically acceptable acid addition salts; and mixtures thereof, and a carrier therefor.

The above compounds are capable of inhibiting the formation of advanced glycosylation endproducts on target proteins. The cross-linking of the protein to form the advanced glycosylation endproduct contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible. Thus, the compounds employed in accordance with this invention inhibit this late-stage Maillard effect and intervene in the deleterious changes described above.

The rationale of the present invention is to use agents which block the post-glycosylation step, i.e., the formation of fluorescent chromophores, the presence of which chromophores is associated with, and leads to adverse sequelae of diabetes and aging. An ideal agent would prevent the formation of the chromophore and its associate cross-links of proteins to proteins and trapping of proteins on the other proteins, such as occurs in arteries and in the kidney.

The chemical nature of the early glycosylation products with which the compounds of the present invention are believed to react may vary, and accordingly the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", *J. Biol. Chem.*, 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNAase as a model system, which was then examined under varying conditions. In one aspect, the glycosylated protein material was isolated and placed in a glucose-free environment and thereby observed to determine the extent of cross-linking.

Eble et al. thereby observed that cross-linking continued to occur not only with the glycosylated protein but with non-glycosylated proteins as well. One of the observations noted by Eble et al. was that the reaction between glycosylated protein and the protein material appeared to occur at the location on the protein chain of the amino acid lysine. Confirmatory experimentation conducted by Eble et al. in this connection demonstrated that free lysine would compete with the lysine on RNAase for the binding of glycosylated protein. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see for example Hayase et al, *J. Biol. Chem.*, 263, pp. 3758–3764 (1989); Sell and Monnier, *J. Biol. Chem.* 264, pp. 21597–21602 (1989); Oimomi et al., *Agric. Biol. Chem.*, 53(6):1727–1728 (1989); and *Diabetes Research and Clinical Practice*, 6:311–313 (1989). Accordingly, the use of lysine as an inhibitor in the Eble et al. model system has no bearing upon the utility of the compounds of the present invention in the inhibition of advanced glycosylated endproducts formation in the presence of glucose in vivo, and the amelioration of complications of diabetes and aging.

The compositions useful in the present invention comprise or contain agents capable of reacting with the active carbonyl intermediate of an early glycosylation product. Suitable agents are the compounds of Formula I of the present invention.

The present invention likewise relates to methods for inhibiting the formation of advanced glycosylation endproducts, which comprise contacting the target proteins with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has, as indicated earlier, been identified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of glucose-derived cross-links. Such diabetic microvascular changes and microvascular occlusion can be effectively prevented by chemical inhibition of advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., *Lab. Invest.*, 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., *Science*, 232, pp. 1629–1632 (1986) to this additional target organ of complication of diabetes. Also, an additional study showed the reduction of immunoglobulin trapping in the kidney by aminoguanidine (Brownlee et al., *Diabetes*, 35, Suppl. 1, p. 42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition of the formation of advanced glycosylation endproducts (AGEs), by the teaching of the present invention, may prevent late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

As noted earlier, the invention also extends to a method of inhibiting the discoloration of teeth resulting from nonenzymatic browning in the oral cavity which comprises administration to a subject in need of such therapy an amount effective to inhibit the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, *J. Dent. Res.*, 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit the formation of advanced glycosylation endproducts. This amount will, of course, vary with the particular agent being utilized and the particular dosage form, but typically is in the range of 0.01% to 1.0%, by weight, of the particular formulation.

The compounds encompassed by Formula I are conveniently prepared by chemical syntheses well-known in the art. Certain of the compounds encompassed by Formula I are well-known compounds readily available from chemical supply houses and/or are preparable by synthetic methods specifically published therefor. For instance, methyl glyoxal bis(guanylhydrazone)dihydrobromide hydrate is obtainable from Aldrich Chem. Co.

Compounds described in the chemical and patent literature or directly preparable by methods described therein and encompassed by Formula I are those such as methyl glyoxal bis (guanylhydrazone) and its biologically or pharmaceutically acceptable acid or alkali addition salts.

Certain of the compounds of formula (I) are novel compounds, not heretofore known in the art. These compounds are those represented by the formula (Ia)

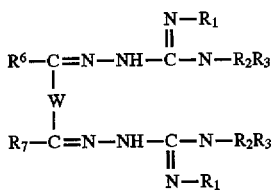

wherein

R₁ and R₂ are each hydrogen or, together, are an alkylene group of 2–3 carbon atoms, or, when R₁ is hydrogen, then R₂ can be a group of the formula

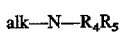

wherein alk is a straight or branched chain alkylene group of 1–8 carbon atoms, and R₄ and R₅ are independently each a lower alkyl group of 1–6 carbon atoms, or together with the nitrogen atom form a morpholino, piperdinyl or methylpiperazinyl group;

R₃ is hydrogen, or when R₁ and R₂ are together an alkylene group of 2–3 carbon atoms, a hydroxyethyl group;

W is a carbon-carbon bond or an alkylene group of 1–3 carbon atoms, and R₆ is a lower alkyl, aryl, or heteroaryl group and R₇ is hydrogen, a lower alkyl, aryl or heteroaryl group; with the proviso that when W is a carbon-carbon bond, then R₆ and R₇ together can also be a 1,4-butylene group; and with the further proviso that when W is a carbon-carbon bond and R₆ or R₇ is lower alkyl, then at least one of R₁, R₂, and R₃ must be other than hydrogen;

or W is a 1,2-, 1,3-, or 1,4-phenylene group, optionally substituted by one or two lower alkyl or amino groups, a 2,3-naphthylene group; a 2,5-thiophenylene group; or a 2,6-pyridylene group; and R₆ and R₇ are both hydrogen or a lower alkyl group;

or W is an ethylene group and R₆ and R₇ together are an ethylene group;

or W is an ethenylene group and R₆ and R₇ together are an ethenylene group;

or W is a methylene group and R₆ and R₇ together are a group of the formula

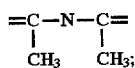

or —C—W—C— and R₆ and R₇ together form a bicyclo (3,3,1)-nonane or a bicyclo-3,3,1-octane group and R₁ and R₂ are together an alkylene group of 2–3 carbon atoms and R₃ is hydrogen;

and their biologically or pharmaceutically acceptable acid addition salts; and mixtures thereof, and a carrier therefor.

The compounds of formula I and Ia can be prepared according to the methods described in Oliverio et al., *J. Pharm. Sci.*, 52:2, pp. 202–203 (1963) or as shown in Scheme I below.

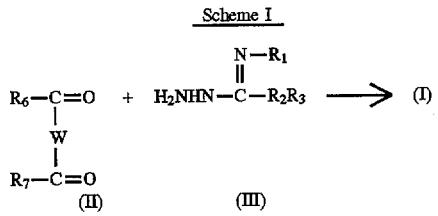

In this reaction Scheme, the appropriate dioxo compound of formula II wherein W, R₆, and R₇ are as hereinbefore defined, is reacted with the appropriate salt of a hydrazine of formula III wherein R₁, R₂ and R₃ are as hereinbefore defined, to afford the desired compound of formula I wherein W, R₁, R₂, R₃, R₆ and R₇ are as hereinbefore defined.

Typically, this reaction is conducted at temperatures of about −5° to about 0° for times of 1–3 hours. Typically, a polar solvent such as ethanol is utilized for the conduct of the reaction, and a nonpolar solvent such as acetone utilized to precipitate the final product.

The following examples are illustrative of the invention.

EXAMPLE 1

Methyl glyoxal bis-(2-hydrazino-2-imidazoline hydrazone)

To the cooled (0°) reaction mixture of 2-hydrazino-2-imidazoline hydrobromide (2.75 g., 15.19 mmole) in ethanol (10 ml) is added, dropwise, methyl glyoxal (2.16 ml, 25.65 mmole) in ethanol (4 ml). The mixture is then stirred at 0° for one hour and then diluted with acetone (75 ml) to afford a white precipitate of the title product. After stirring this mixture at room temperature for two hours, the precipitate is filtered, dried and crystallized from ethanol and a few drops of water to give pure methyl glyoxal bis(2-hydrazino-2-imidazoline hydrazone) dihydrobromide (1.21 g.), m.p. 256°–257° C.

EXAMPLE 2

Using the appropriate dioxo compounds of formula II with the appropriate hydrazine of formula III in accordance with the procedures detailed in Example 1, the following compounds of Formula I are synthesized.

Compound of Formula I methyl glyoxal bis(guanylhydrazone)dihydrochloride hydrate, m.p. 255° C. (dec.);

terephthaldicarboxaldehyde bis(2-hydrazino-2-imidazoline hydrazone)dihydrobromide monohydrate, m.p. >350° C.;

terephthaldicarboxaldehyde bis(guanylhydrazone) dihydrochloride monohydrate, m.p. 320°–322° C. (dec.);

phenyl glyoxal bis(2-hydrazino-2-imidazoline hydrazone) dihydrobromide monohydrate, m.p. 260°–261° C.;

furyl glyoxal bis(2-hydrazino-2-imidazoline hydrazone) dihydrobromide dihydrate, m.p. 223°–225° C.;

methyl glyoxal bis[1-(2-hydroxyethyl)-2-hydrazino-2-imidazoline hydrazone]dimethanesulfonate, m.p. 206°–207° C.;

methyl glyoxal bis[1-(2-hydroxyethyl)-2-hydrazino-1,4,5,6-tetrahydropyrimidine hydrazone]dimethanesulfonate, m.p. 214°–215° C.;

phenyl glyoxal bis(guanylhydrazone)dihydrochloride, m.p. 243°–245° C. (dec.);

phenyl glyoxal bis[1-(2-hydroxyethyl)-2-hydrazino-2-imidazoline hydrazone]dimethanesulfonate dihydrate, m.p. 94°–95° C.;

furyl glyoxal bis[1-(2-hydroxyethyl)-2-hydrazino-2-imidazoline hydrazone]dimethanesulfonate monohydrate, m.p. 162°–163° C.;

phenyl glyoxal bis[1-(2-hydroxyethyl)-2-hydrazino-1,4,5,6-tetrahydropyrimidine hydrazone]dimethanesulfonate dihydrate, m.p. 162°–165° C.;

furyl glyoxal bis[1-(2-hydroxyethyl)-2-hydrazino-1,4,5,6-tetrahydropyrimidine hydrazone]dimethanesulfonate dihydrate, m.p. 139°–140° C. (dec.);

2,3-butanedione bis(2-hydrazino-2-imidazoline hydrazone) dihydrobromide monohydrate, m.p. 286°–287° C. (dec.);

1,4-cyclohexane dione bis(2-hydrazino-2-imidazoline hydrazone]dihydrobromide dihydrate, m.p. 243° C. (dec.);

o-phthalicdicarboxaldehyde bis(2-hydrazino-2-imidazoline hydrazone)dihydrobromide monohydrate, m.p. 216°–217° C.;

2,3-naphthalene dialdehyde bis(2-hydrazino-2-imidazoline hydrazone)dihydrobromide dihydrate, m.p. 256°–257° C. (dec.);

1,2-cyclohexanedione bis(2-hydrazino-2-imidazoline hydrazone)dihydrobromide dihydrate, m.p. 283°–285° C.;

2,4-pentanedione bis(2-hydrazino-2-imidazoline hydrazone)dihydrobromide, m.p. 219°–220° C.;

furyl bis(2-hydrazino-2-imidazoline hydrazone) dihydrobromide, dihydrobromide, m.p. 208°–209° C. (dec.);

1,4-benzoquinone bis(2-hydrazino-2-imidazoline hydrazone) dihydrobromide, m.p. >350° C.;

methyl glyoxal bis(2-hydrazino-1,4,5,6-tetrahydropyrimidine hydrazone)dihydrobromide, m.p. 258°–261° C. (dec.);

methyl glyoxal bis[N-(2,2-dimethyl-3-dimethylaminopropyl)hydrazinecarboximidamide hydrazone]tetrahydrobromide, m.p. 101°–103° C.;

methyl glyoxal bis[N-3-dimethylaminopropyl)hydrazinecarboximidamide hydrazone] tetrahydrobromide, m.p. 218°–220° C.;

methylglyoxal bis{N-[2-(4-morpholino)ethyl]hydrazinecarboximidamide hydrazone}tetrahydrobromide, m.p. 267°–269° C.;

methyl glyoxal bis{N-[3-(4-methylpeperazin-1-yl)propyl]hydrazinecarboximidamide hydrazone}hexahydrobromide, m.p. 249°–250° C. (dec.).

furyl glyoxal bis (guanyl hydrazone)dihydrochloride dihydrate, m.p. 84°–86° C.;

2,3-pentanedione bis(2-tetrahydropyrimidine)hydrazone dihydrobromide, m.p. 288°–290° C. (dec.);

1,2-cyclohexanedione bis(2-tetrahydropyrimidine)hydrazone dihydrobromide, m.p. 205°–208° C.;

2,3-hexanedione bis(2-tetrahydropyrimidine)hydrazone dihydrobromide, m.p. 268°–270° C.;

1,3-diacetyl bis(2-tetrahydropyrimidine)hydrazone dihydrobromide, m.p. >300° C.;

2,3-butanedione bis(2-tetrahydropyrimidine)hydrazone dihydrobromide, m.p. 305°–307° C. (dec);

2,6-diacetylpyridine-bis-(2-hydrazino-2-imidazoline hydrazone)dihydrobromide, m.p. >350° C.;

2,6-diacetylpyridine-bis-(guanyl hydrazone) dihydrochloride, m.p. >350° C.;

2,6-pyridine dicarboxaldehyde-bis-(2-hydrazino-2-imidazoline hydrazone)dihydrobromide trihydrate), m.p. 310°–311° C. (dec);

2,6-pyridine dicarboxaldehyde-bis(guanylhydrazone) dihydrochloride, m.p. 305°–306° C. (dec);

1,4-diacetyl benzene-bis-(2-hydrazino-2-imidazoline hydrazone)dihydrobromide dihydrate, m.p. >350° C.;

1,3-diacetyl benzene-bis-(2-hydrazino-2-imidazoline) hydrazone dihydrobromide, m.p. >350° C.;

1,3-diacetyl benzene-bis(guanyl)-hydrazone dihydrochloride, m.p. 318°–320° C. (dec);

isophthalaldehyde-bis-(2-hydrazino-2-imidazoline) hydrazone dihydrobromide, m.p. 290°–292° C.;

isophthalaldehyde-bis-(guanyl)hydrazone dihydrochloride, m.p. 286°–287° C.;

2,6-diacetylaniline bis-(guanyl)hydrazone dihydrochloride, m.p. 133°–134° C.;

2,6-diacetyl aniline bis-(2-hydrazino-2-imidazoline) hydrazone dihydrobromide, m.p. 234°–236° C.;

2,5-diacetylthiophene bis(guanyl)hydrazone dihydrochloride, m.p. 1778°–179° C.;

2,5-diacetylthiophene bis-(2-hydrazino-2-imidazoline) hydrazone dihydrobromide, m.p. 175°–179 C. (dec);

1,4-cyclohexanedione bis(2-tetrahydropyrimidine) hydrazone dihydrobromide, m.p. 153°–155° C. (dec);

3,4-hexanedione bis(2-tetrahydropyrimidine)hydrazone dihydrobromide, m.p. 296°–299° C. (dec);

methyl glyoxal-bis-(4-amino-3-hydrazino-1,2,4-triazole) hydrazone dihydrochloride, m.p. 245°–246° C. (dec);

methyl glyoxal-bis-(4-amino-3-hydrazino-5-methyl-1,2,4-triazole)hydrazone dihydrochloride, m.p. 245°–246° C. (dec);

2,3-pentanedione-bis-(2-hydrazino-3-imidazoline) hydrazone dihydrobromide, m.p. 92°–93° C.;

2,3-hexanedione-bis-(2-hydrazino-2-imidazoline) hydrazone dihydrobromide, m.p. 242°–244° C (dec);

3-ethyl-2,4-pentane dione-bis-(2-hydrazino-2-imidazoline) hydrazone dihydrobromide, m.p. 210°–212° C.;

methyl glyoxal-bis-(4-amino-3-hydrazino-5-ethyl-1,2,4-triazole)hydrazone dihydrochloride, m.p. 233°–234° C. (dec);

methyl glyoxal-bis-(4-amino-3-hydrazino-5-isopropyl-1,2,4-triazole)hydrazone dihydrochloride, m.p. 230°–232° C. (dec);

methyl glyoxal-bis-(4-amino-3-hydrazino-5-cyclopropyl-1,2,4-triazole)hydrazone dihydrochloride, m.p. 210°–212° C. (dec);

methyl glyoxal-bis-(4-amino-3-hydrazino-5-cyclobutyl-1,2,4-triazole)hydrazone dihydrochloride, m.p. 234°–235° C. (dec);

1,3-cyclohexanedione-bis-(2-hydrazino-2-imidazoline) hydrazone dihydrobromide, m.p. 262°–264° C.;

3,5-diacetyl-1,4-dihydro-2,6-dimethyl pyridine bis(guanyl) hydrazone dihydrochloride, m.p. 177–178° C. (dec);

3,5-diacetyl-1,4-dihydro-2,6-dimethyl pyridine bis-(2-hydrazino-2-imidazoline)hydrazone dihydrobromide, m.p. 171°–173° C. (dec);

bicyclo-(3,3,1)nonane-3,7-dione bis-(2-hydrazino-2-imidazoline)hydrazone dihydrobromide, m.p. 175°–177° C.; and cis-bicyclo(3,3,1)octane-3,7-dione bis-(2-hydrazino-2-imidazoline) hydrazone dihydrobromide, m.p. 298°–299° C. (dec).

EXAMPLE 3

The following method was used to evaluate the ability of the compounds of the present invention to inhibit the cross-linking of glycated bovine serum albumin (AGE-BSA) to the rat tail tendon collagen coated 96-well plate.

The AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PAS) for 48 hours with additional 5 times buffer exchanges. The rat tail tendon collagen coated plate was blocked first with 300 μl of superbloc blocking buffer (Pierce #37515X) for one hour. The blocking solution was removed from the wells by washing the plate twice with PAS-Tween 20 solution (0.05% Tween 20) using a NUNC-multiprobe or Dynatech ELISA-plate washer. Cross-linking of AGE-BSA (1 to 10 μg per well depending on the batch of AGE-BSA) to rat tail tendon collagen coated plate was performed with and without the testing compound dissolved in PAS buffer at pH 7.4 at the desired concentrations by the addition of 50 μl each of the AGE-BSA diluted in PAS or in the testing compound at 37° C. for 4 hours. The unbrowned BSA in PAS buffer with or without testing compound were added to the separate wells as the blanks. The un-cross-linked AGE-BSA was then removed by washing the wells three times with PAS-Tween buffer. The cross-linked AGE-BSA to the tail tendon coated plate was then quantitated by the polyclonal antibody raised against AGE-RNase. After a one-hour incubation period, AGE antibody was removed by washing 4 times with PAS-Tween.

The bound AGE antibody was then detected with the addition of horseradish peroxidase-conjugated secondary antibody, e.g., goat anti-rabbit immunoglobulin and incubation for 30 minutes. The substrate of 2,2-azino-di(3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

% inhibition={[Optical density (without compound)−optical density (with compound)]/optical density (without compound)} 100%

The $IC_{50}$ relative inhibition by various test compounds at 10 Mm is as follows:

| Test Compound | $IC_{50}$ |
|---|---|
| methyl glyoxal bis(2-hydrazino-2-imidazoline hydrazone) dihydrobromide monohydrate | 2.04 ± 0.05 |
| phenyl glyoxal bis(2-hydrazino-2-imidazoline hydrazone)dihydrobromide monohydrate | 0.05 |
| furyl glyoxal bis(2-hydrazino-2-imidazoline hydrazone) dihydrobromide dihydrate | 0.12 ± 0.10 |
| methyl glyoxal bis[1-(2-hydroxyethyl)-2-hydrazino-2-imidazoline hydrazone] dimethanesulfonate | 0.32 ± 0.07 |
| methyl glyoxal bis[1-(2-hydroxyethyl)-2-hydrazino-1,4,5,6-tetrahydropyrimidine hydrazone] dimethanesulfonate | 0.17 ± 0.11 |
| phenyl glyoxal bis(guanyl hydrazone) dihydrochloride | 0.34 ± 0.19 |
| phenyl glyoxal bis[1-(2-hydroxyethyl)-2-hydrazino-2-imidazoline hydrazone] dimethanesulfonate dihydrate | 0.09 ± 0.13 |
| furyl glyoxal bis[1-(2-hydroxyethyl)-2-hydrazino-2-imidazoline hydrazone dimethanesulfonate monohydrate | 0.92 ± 0.26 |
| phenyl glyoxal bis[1-(2-hydroxyethyl)-2-hydrazino-1,4,5,6-tetrahydropyrimidine hydrazone] dimethanesulfonate dihydrate | 0.07 ± 0.10 |
| furyl glyoxal bis[1-(2-hydroxyethyl)-2-hydrazino-1,4,5,6-tetrahydropyrimidine hydrazone]dimethanesulfonate dihydrate | 0.02 ± 0.09 |
| 1,4-cyclohexane dione bis(2-hydrazino-2-imidazoline hydrazone] dihydrobromide dihydrate | 0.10 + 0.17 |
| o-phthalic dicarboxaldehyde bis(2-hydrazino-2-imidazoline hydrazone) dihydrobromide monohydrate | 0.43 ± 0.08 |
| 2,3-naphthalene dialdehyde bis(2-hydrazino-2-imidazoline hydrazone) dihydrobromide dihydrate | 0.03 ± 0.25 |
| 1,2-cyclohexanedione bis(2-hydrazino-2-imidazoline hydrazone) dihydrobromide dihydrate | 0.01 ± 0.17 |
| 2,4-pentanedione bis(2-hydrazino-2-imidazoline hydrazone) dihydrobromide | 0.04 ± 0.33 |
| furyl bis (2-hydrazino-2-imidazoline hydrazone) dihydrobromide | 0.02 ± 0.13 |
| 1,4-benzoquinone bis(2-hydrazino-2-imidazoline hydrazone) dihydrobromide | 0.02 ± 0.14 |
| methyl glyoxal bis(2-hydrazino-1,4,5,6-tetrahydropyrimidine hydrazone) dihydrobromide | 0.84 ± 0.12 |
| methyl glyoxal bis[N-(2,2-dimethyl-3-dimethylaminopropyl) hydrazinecarboximidamide hydrazone] tetrahydrobromide | 0.44 ± 0.06 |
| methyl glyoxal bis[N-3-dimethylaminopropyl)hydrazinecarboximidamide hydrazone] tetrahydrobromide | 0.22 ± 0.05 |
| methyl glyoxal bis[N-[2-(4-morpholino)ethyl(hydrazinecarboximidamide hydrazone] tetrahydrobromide | 2.20 ± 0.13 |
| furyl glyoxal bis (guanyl hydrazone)dihydrochloride dihydrate | 0.31 |
| 1,2-cyclohexanedione bis(2-tetrahydropyrimidine)hydrazone dihydrobromide | 0.0067 |
| 2,3-hexanedione bis (2-tetrahydropyrimidine)hydrazone dihydrobromide | 0.033 |
| 2,3-butanedione bis(2-tetrahydropyrimidine)hydrazone dihydrobromide | 0.0041 |
| methyl glyoxal-bis-(4-amino-3-hydrazino-5-ethyl-1,2,4-triazole)hydrazone dihydrochloride | 0.12 |
| methyl glyoxal-bis-(4-amino-3-hydrazino-5-isopropyl-1,2,4-triazole)hydrazone dihydrochloride. | 0.11 |

The above experiments suggest that this type of drug therapy may have benefit in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 4

| Tablet | mg/tablet |
| --- | --- |
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a $^{11}/_{32}$" punch with a hardness of 4 kg. These tablets will disintegrate within a half hour according to the method described in USP XVI.

EXAMPLE 5

| Lotion | mg/g |
| --- | --- |
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 6

| Oral Rinse | |
| --- | --- |
| Compound of Formula I: | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 7

| Toothpaste | |
| --- | --- |
| Compound of Formula I: | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | 0.76% |
| Dibasic calcium phosphate dihydrate | 45% |
| Water to | 100% |

EXAMPLE 8

To further study the ability of inhibitors of nonenzymatic browning to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 Mm glucose-6-phosphate in a 0.5M phosphate buffer, Ph 7.4, containing 3 Mm sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed.

Incubation of the disks in glucose-6-phosphate alone shows slight brown color versus disks soaked in buffer alone. Inclusion of chlorhexidine (in the form of Peridex® at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for inhibiting the advanced glycosylation of a target protein comprising contacting the target protein with an effective amount of a composition comprising a compound selected from the group consisting of compounds of the formula

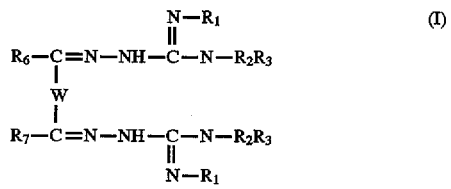

wherein $R_1$ and $R_2$ are together an alkylene group of 2–3 carbon atoms;

$R_3$ is hydrogen or a hydroxyethyl group;

W is a carbon-carbon bond or an alkylene group of 1–3 carbon atoms, and $R_6$ is a lower alkyl, aryl, or heteroaryl group, and $R_7$ is hydrogen, a lower alkyl, aryl or heteroaryl group, with the proviso that when W is a carbon-carbon bond, then $R_6$ and $R_7$ together can also be a 1,4-butylene group; and their biologically or pharmaceutically acceptable acid addition salts; and mixtures thereof, and a carrier therefor.

2. The method of claim 1 wherein said compound has the formula wherein W is carbon-carbon bond.

3. The method of claim 2 wherein said compound is methyl glyoxal bis(2-hydrazino-1,4,5,6- tetrahydropyrimidine hydrazone) dihydrobromide or another pharmaceutically acceptable salt thereof.

4. The method of claim 1 wherein said compound has the formula wherein W is a methylene group.

5. A method for treating an animal to inhibit the formation of advanced glycosylation endproducts of a target protein within said animal, said method comprising administering to said animal an effective amount of a pharmaceutical composition, said pharmaceutical composition comprising a compound selected from the group consisting of compounds of the formula

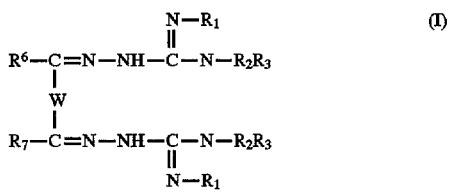

wherein $R_1$ and $R_2$ are together an alkylene group of 2–3 carbon atoms;

$R_3$ is hydrogen or a hydroxyethyl group;

W is a carbon-carbon bond or an alkylene group of 1–3 carbon atoms, and $R_6$ is a lower alkyl, aryl, or heteroaryl group, and $R_7$ is hydrogen, a lower alkyl, aryl or heteroaryl group, with the proviso that when W is a carbon-carbon bond, then $R_6$ and $R_7$ together can also be a 1,4-butylene group, and with the further proviso that when W is a carbon-carbon bond and $R_6$ is an alkyl group, then $R_7$ is hydrogen; and their biologically or pharmaceutically acceptable acid addition salts; and mixtures thereof, and a carrier therefor.

6. The method of claim 5 wherein said compound has the formula wherein W is carbon-carbon bond.

7. The method of claim 6 wherein said compound is methyl glyoxal bis(2-hydrazino-1,4,5,6-tetrahydropyrimidine hydrazone) dihydrobromide or another pharmaceutically acceptable salt thereof.

8. The method of claim 5 wherein said compound has the formula wherein W is a methylene group.

9. A method of inhibiting the discoloration of teeth resulting from non-enzymatic browning in the oral cavity which comprises administration to said oral cavity of an amount effective to inhibit the formation of advanced glycosylation endproducts of a composition comprising a compound selected from the group consisting of compounds of the formula

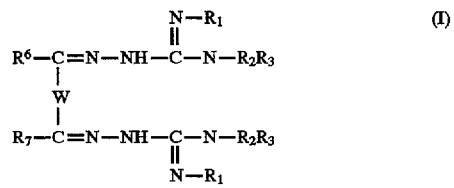

wherein $R_1$ and $R_2$ are an alkylene group of 2–3 carbon atoms;

$R_3$ is hydrogen or a hydroxyethyl group;

W is a carbon-carbon bond or an alkylene group of 1–3 carbon atoms, and $R_6$ is a lower alkyl, aryl, or heteroaryl group and $R_7$ is hydrogen, a lower alkyl, aryl or heteroaryl group, with the proviso that when W is a carbon-carbon bond, then $R_6$ and $R_7$ together can also be a 1,4-butylene group; and their biologically or pharmaceutically acceptable acid addition salts; and mixtures thereof, and a carrier therefor.

10. The method of claim 9 wherein said compound has the formula wherein W is carbon-carbon bond.

11. The method of claim 10 wherein said compound is methyl glyoxal bis(2-hydrazino-1,4,5,6-tetrahydropyrimidine hydrazone) dihydrobromide or another pharmaceutically acceptable salt thereof.

12. The method of claim 9 wherein said compound has the formula wherein W is a methylene group.

13. The method of claim 1 in which the compound is methyl glyoxal bis(2-hydrazino-2-imidazoline hydrazone) dihydrobromide monohydrate or another pharmaceutically acceptable salt thereof.

14. The method of claim 1 in which the compound is phenyl glyoxal bis(2-hydrazino-2-imidazoline)hydrazone dihydrobromide monohydrate or another pharmaceutically acceptable salt thereof.

15. The method of claim 1 which the compound is furyl glyoxal bis(2-hydrazino-2-imidazoline hydrazone) dihydrobromide dihydrate or another pharmaceutically acceptable salt thereof.

16. The method of claim 1 in which the compound is methyl glyoxal bis[1-(2-hydroxyethyl)-2-hydrazino-2-imidazoline hydrazone]dimethanesulfonate or another pharmaceutically acceptable salt thereof.

17. The method of claim 1 in which the compound is methyl glyoxal bis[1-(2-hydroxyethyl)-2-hydrazino-1,4,5,6-tetrahydropyrimidine hydrazone]dimethanesulfonate or another pharmaceutically acceptable salt thereof.

18. The method of claim 1 in which the compound is phenyl glyoxal bis[1-(2-hydroxyethyl)-2-hydrazino-2-imidazoline hydrazone]dimethanesulfonate dihydrate or another pharmaceutically acceptable salt thereof.

19. The method of claim 1 in which the compound is furyl glyoxal bis[1-(2-hydroxyethyl)-2-hydrazino-2-imidazoline hydrazone)dimethanesulfonate monohydrate or another pharmaceutically acceptable salt thereof.

20. The method of claim 1 in which the compound is phenyl glyoxal bis[1-(2-hydroxyethyl)-2-hydrazino-1,4,5,6-tetrahydropyrimidine hydrazone]dimethanesulfonate dihydrate or another pharmaceutically acceptable salt thereof.

21. The method of claim 1 in which the compound is furyl glyoxal bis[1-(2-hydroxyethyl)-2-hydrazino-1,4,5,6-tetrahydropyrimidine hydrazone]dimethanesulfonate dihydrate or another pharmaceutically acceptable salt thereof.

22. The method of claim 1 in which the compound is 1,2-cyclohexanedione bis(2-hydrazino-2-imidazoline hydrazone) dihydrobromide dihydrate or another pharmaceutically acceptable salt thereof.

23. The method of claim 1 in which the compound is 2,4-pentanedione bis(2-hydrazino-2-imidazoline hydrazone) dihydrobromide or another pharmaceutically acceptable salt thereof.

24. The method of claim 1 in which the compound is furyl bis(2-hydrazino-2-imidazoline hydrazone) dihydrobromide or another pharmaceutically acceptable salt thereof.

25. The method of claim 1 in which the compound is 1,2-cyclohexanedione bis(2-tetrahydropyrimidine) hydrazone dihydrobromide.

26. The method of claim 1 in which the compound is 2,3-hexanedione bis(2-tetrahydropyrimidine)hydrazone dihydrobromide.

27. The method of claim 1 in which the compound is 2,3-butanedione bis(2-tetrahydropyrimidine)hydrazone dihydrobromide.

* * * * *